United States Patent [19]
Kost et al.

[11] Patent Number: 6,041,253
[45] Date of Patent: *Mar. 21, 2000

[54] EFFECT OF ELECTRIC FIELD AND ULTRASOUND FOR TRANSDERMAL DRUG DELIVERY

[75] Inventors: Joseph Kost, Omer, Israel; Uwe Pliquett, Leipzig, Germany; Samir S. Mitragotri, Somerville, Mass.; Robert S. Langer, Newton, Mass.; James C. Weaver, Sudbury, Mass.

[73] Assignee: Massachusetts Institute of Technology, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/626,021

[22] Filed: Apr. 1, 1996

Related U.S. Application Data

[63] Continuation-in-part of application No. 08/574,377, Dec. 18, 1995.

[51] Int. Cl.[7] ..................................................... A61N 1/30
[52] U.S. Cl. .............................. 604/20; 604/22; 600/578
[58] Field of Search .................................. 604/20, 22, 49; 601/2; 128/760, 637; 600/573, 578

[56] References Cited

U.S. PATENT DOCUMENTS

| | | |
|---|---|---|
| 3,551,554 | 12/1970 | Herschler . |
| 3,711,602 | 1/1973 | Herschler . |
| 3,711,606 | 1/1973 | Herschler . |
| 4,002,221 | 1/1977 | Buchalter . |
| 4,127,125 | 11/1978 | Takemoto et al. . |
| 4,144,646 | 3/1979 | Takemoto et al. . |
| 4,176,664 | 12/1979 | Kalish . |
| 4,249,531 | 2/1981 | Hiller et al. . |
| 4,280,494 | 7/1981 | Cosgrove, Jr. et al. . |
| 4,309,989 | 1/1982 | Fahim . |

(List continued on next page.)

FOREIGN PATENT DOCUMENTS

| | | |
|---|---|---|
| 43738 B1 | 10/1985 | European Pat. Off. . |
| 368408 | 5/1990 | European Pat. Off. . |
| 612525 A1 | 8/1994 | European Pat. Off. . |
| 27 56 460A1 | 6/1979 | Germany . |
| 3-170172 | 7/1991 | Japan . |
| 445433 | 11/1974 | U.S.S.R. . |
| 556805 | 6/1977 | U.S.S.R. . |
| 591186 | 1/1978 | U.S.S.R. . |
| 0910157 | 2/1978 | U.S.S.R. . |
| 506421 | 2/1978 | U.S.S.R. . |
| 1 577 551 | 2/1976 | United Kingdom . |
| 2153223 | 8/1985 | United Kingdom . |
| WO 88/00001 | 1/1988 | WIPO . |
| WO 90/01971 | 3/1990 | WIPO . |
| WO 90/15568 | 12/1990 | WIPO . |
| WO 91/12772 | 9/1991 | WIPO . |
| WO 93/20745 | 10/1993 | WIPO . |

OTHER PUBLICATIONS

Apfel, R. E., "Possiblity of Microcavitation from Diagnostic Ultrasound," *IEEE Trans. Ultrason, Ferroelectrics Freq. Control* UFFC–33:139–142 (1986).

(List continued on next page.)

*Primary Examiner*—Mark Bockelman
*Attorney, Agent, or Firm*—Arnall Golden & Gregory, LLP

[57] ABSTRACT

Transdermal transport of molecules during sonophoresis (delivery or extraction) can be further enhanced by application of an electric field, for example, electroporation or iontophoresis. In a preferred embodiment the ultrasound is low frequency ultrasound which induces cavitation of the lipid layers of the stratum corneum (SC). This method provides higher drug transdermal fluxes, allows rapid control of transdermal fluxes, and allows drug delivery or analyte extraction at lower ultrasound intensities than when ultrasound is applied in the absence of an electric field.

10 Claims, 4 Drawing Sheets

U.S. PATENT DOCUMENTS

| | | |
|---|---|---|
| 4,372,296 | 2/1983 | Fahim . |
| 4,537,776 | 8/1985 | Cooper . |
| 4,557,943 | 12/1985 | Rosler et al. . |
| 4,563,184 | 1/1986 | Korol . |
| 4,595,011 | 6/1986 | Phillips . |
| 4,646,725 | 3/1987 | Moasset . |
| 4,698,058 | 10/1987 | Greenfeld et al. . |
| 4,732,153 | 3/1988 | Phillips . |
| 4,767,402 | 8/1988 | Kost et al. . |
| 4,780,212 | 10/1988 | Kost et al. . |
| 4,787,888 | 11/1988 | Fox . |
| 4,820,720 | 4/1989 | Sanders et al. . |
| 4,821,733 | 4/1989 | Peck . |
| 4,821,740 | 4/1989 | Tachibana et al. . |
| 4,834,978 | 5/1989 | Nuwayser . |
| 4,855,298 | 8/1989 | Yamada et al. . |
| 4,860,058 | 8/1989 | Kobayashi et al. . |
| 4,863,970 | 9/1989 | Patele t al. . |
| 4,953,565 | 9/1990 | Tachibana et al. . |
| 5,006,342 | 4/1991 | Cleary et al. . |
| 5,007,438 | 4/1991 | Tachibana et al. . |
| 5,015,615 | 5/1991 | Driller . |
| 5,019,034 | 5/1991 | Weaver et al. ............................ 604/20 |
| 5,076,273 | 12/1991 | Schoendorfer et al. . |
| 5,115,805 | 5/1992 | Bommannan et al. . |
| 5,139,023 | 8/1992 | Stanley et al. . |
| 5,140,985 | 8/1992 | Stanley et al. . |
| 5,171,215 | 12/1992 | Flanagan . |
| 5,197,946 | 3/1993 | Tachibana . |
| 5,231,975 | 8/1993 | Bammannan et al. ..................... 604/20 |
| 5,267,985 | 12/1993 | Shimada et al. . |
| 5,315,998 | 5/1994 | Tachibana et al. . |
| 5,323,769 | 6/1994 | Bommannan et al. . |
| 5,386,837 | 2/1995 | Sterzer . |
| 5,401,237 | 3/1995 | Tachibana et al. . |
| 5,405,614 | 4/1995 | D'Angelo et al. . |
| 5,415,629 | 5/1995 | Henley ...................................... 604/20 |
| 5,421,816 | 6/1995 | Lipkovker . |
| 5,443,080 | 8/1995 | D'Angelo . |
| 5,445,611 | 8/1995 | Eppstein et al. .......................... 604/49 |
| 5,458,140 | 10/1995 | Eppstein et al. . |
| 5,582,586 | 12/1996 | Tachibana et al. ....................... 604/22 |
| 5,617,851 | 4/1997 | Lipkovker . |
| 5,658,247 | 8/1997 | Henley ...................................... 604/20 |

OTHER PUBLICATIONS

Aungst, et al., "Contributions of Drug Solubilization, Partitioning, Barrier Disruption, and Solvent Permeation to the Enhancement of Skin Permeation of Various Compounds with Fatty Acids and Amines," *Pharm. Res.* 7:712–718 (1990).

Barry, "Mode of Action of Penetration Enhancers in Human Skin," *J. Controlled Rel.* 6:85–97 (1987).

Bommer, et al., "Subcutaneous Erythropoeitin," *Lancet* 406 (1988).

Burnette, R. R.,"Iontophoresis," *Transdermal Drug Delivery Developmental Issues and Research Initiatives* (Hadgraft and Guy, Editors, Marcel Dekker, 247–291, 1989).

Cleary, Gary W., "Transdermal Controlled Release Systems," *Medical Applications of Controlled Release* (Langer and Wise, Editors, CRC Press 203–251, 1984).

Clegg and Vaz, "Translational diffusion of proteins and lipids in artificial lipid bilayer membranes. A comparison of experiment with theory," *Progress in Protein–Lipid Interactions* Watts, ed. (Elsvier, NY 1985) Chapter 5:173–229.

Davis, J.,et al., "Characterization of Recombinant Human Erythropoietin Produced in Chinese Hamster Ovary Cells," *Biochemistry* 26:2633–2638 (1987).

Ebert, et al., "Transbuccal Absorption of Diclofenac Sodium in a Dog Model," *Controlled Release Technology Pharmaceutical Application* (Lee, et al. Editors, American Chemical Society)310–321 (1987).

Eggerth, et al., "Evaluation of Hamster Cheek Pouch as a Model for Buccal Absorption," *Proceed. Intern. Symp. Rel. Bioact. Mater.*,(Controlled Release Society, Inc.) 14:180–181 (1987).

D'Emanuele, et al., "An Investigation of the Effects of Ultrasound on Degradable Polyanhydride Matrices," *Macromolecules* 25:511–515 (1992).

Elias, "The Microscopic Structure of the Epidermis and Its Derivatives," *Percutaneous Absorption: Mechanisms—Methodology—Drag Delivery* (Bronaugh, R. L., Maibach, H., Editors, Marcel Dekker, New York,) 1–12 (1989).

*Egorov, E.A. et al., "Use of the Variants of the Pharmacophysical Influence in Ophthalmology", 102 Ophthalmology Journal #2 (1992).

*Eppstein, D.A. et al., "Applications of Liposome Formulations for Antimicrobial/Antiviral Therapy" Liposomes as Drug Carriers 311, 315 (G. Gregoriadis ed. 1988).

*Eppstein, D.A., "Medical Utility of Inteferons: Approaches to Increasing Therapeutic Efficacy" 7 Pharmacy International 195–198 (1986).

*Eppstein, D.A. et al., "Alternative Delivery Systems for Peptides and Proteins as Drugs" 5 CRC Reviews in Therapeutic Drug Carrier Systems 99, 125 (1988).

Flynn, G. L., "Mechanism of Percutaneous Absorption from Physiocochemical Evidence," *Percutaneous Absorption: Mechanisms—Methology—Drug Delivery* (Bronaugh, R. L., Maibach, H., Editors, Marcel Dekker, New York) 27–51 (1989).

Friedman, R. M., '*Inteferons: A Primer*', (Academic Press, New York, 1981).

Gaertner, W., "Frequency Dependence of Ultrasonic Cavitation," *J. Acoust. Soc. Am.* 26:977–980 (1954).

Ghanem et al., "The effects of ethanol on the transport of lipophilic and polar permeants across hairless mouse skin: Methods/validation of a novel approach," *Int. J. Pharm.* 78:137–156 (1992).

Grups and Frohmuller, "Cyclic Inteferon Gamma Treatment of Patients with Metastatic Renal Carcinoma," *J. Med.* 64(3):218–220 (1989).

Hansch and Leo, "Substituent Constants for Correlation Analysis in Chemistry and Biology" (1979).

Junginger, et al., "Visualization of Drug Transport Across Human Skin and the Influence of Penetration Enhancers," *"Drug Permeation Enhancement"* (Hsieh, D.S., Editors, Marcel Dekker, Inc. New York) 59–89 (1994).

Kasting, et al., "Prodrugs for Dermal Delivery: Solubility, Molecular Size, and Functional Group Effects," "Prodrugs: Topical and Ocular Delivery" Sloan, ed. (Marcel Dekker, NY 1992) 117–161.

Kost and Langer, "Ultrasound–Mediated Transdermal Drug Delivery," *Topical Drug Bioavailability Bioequivalence and Penetration* (Maibach, H. I., Shah, V. P., Editors, Plenum Press, New York) 91–104 (1993).

Kost, et al., "Ultrasound Effect on Transdermal Drug Delivery," (Ben Gurion University Dept. of Chem. Engineering, Beer Sheva Israel) (MIT, Dept. of Applied Biological Sciences, Cambridge, MA) CRS Aug. 1986.

Krall, L.P., 'World Book of Diabetes in Practice' (Editors, Elsvier, 1988).

Lee, V. H. L., et al., "Protease Inhibition as an Additional Mechanism for the Nasal Absorption Enhancement Effect of Sodium Taurodihydrofusidate," *Proceed. Intern. Symp. Control. Rel. Bioact. Mater.* 14:55–56 (1987).

Lee, V. H. L., et al., "Nasal Peptide and Protein Absorption Promoters: Aminopeptidase Inhibtion as a Predictor of Absorption Enhancement Potency of Bile Salts," *Proceeds. Intern. Symp. Control. Rel. Bioact. Mater* 14:53–54 (1987).

Levy, et al., "Effect of Ultrasound on Transdermal Drug Delivery to Rats and Guinea Pigs," *J. Clin. Invest.* 83:2074–2078 (1989).

Liu, et al., "Cotransport of Estradiol and Ethanol Through Human Skin In Vitro: Understanding the Permeant/Enhancer Flux Relationship," *Pharmaceutical Research* 8:938–944 (1991).

Liu, et al., "Experimental Approach To Elucidate the Mechanism of Ultrasound–Enhanced Polymer Erosion and Release of Incorporated Substances," *Macromolecules* 25:123–128 (1992).

*Loshilov, V.I. et al., "Research of the Technological Process of Ultrasound Treatment of Infected Wounds" (1976).

Machluf and Kost, "Ultrasonically enhanced transdermal drug delivery. Experimental approaches to elucidate the mechanism," *J. Biomater. Sci. Polymer Edn.* 5:147–156 (1993).

Mak, et al., "Oleic Acid Concentration and Effect in Human Statum Corneum: Non–Invasive Determination by Attenuated Total Reflectance Infrared Spectroscopy In Vivo," *J. Controlled Rel.* 12:67–75 (1990).

Mitragotri, et al., "Ultrasound–Mediated Transdermal Protein Delivery," *Science* 269:850–853 (1995).

Mitragotri, et al., "A Mechanistic Study of Ultrasonically–Enhanced Transdermal Drug Delivery," *J. Pharm. Sci.* 84:697–706 (1995).

Morimoto, Y., et al., "Prediction of Skin Permeability of Drugs: Comparison of Human and Hairless Rat Skin," *J. Pharm. Pharmacol.* 44:634–639 (1991).

Nagai and Konishi, "Buccal/Gingival Drug Delivery Systems," *Journal of Controlled Release* (Elsevier Science Publishers B.V., Amsterdam) 6:353–360 (1987).

Newman, J., et al., "Hydrocortisone Phonophoresis," *J. Am. Pod. Med. Assoc.* 82:432–435 (1992).

Olanoff and Gibson, "Method to Enhance Intranasal Peptide Delivery," *Controlled Release Technology Pharmaceutical Application* (Lee, et al. Editors, American Chemical Society) 301–309 (1987).

Ongpipattanankul, et al., "Evidence that Oleic Acid Exists in a Separate Phase Within Statum Corneum Lipids," *Pharm. Res.* 8:350–354 (1991).

Parkin, et al., "Atopic manifestations in the acquired immune deficiency syndrome: response to recombinant interferon gamma," *Br. Med. J.*, 294:1185–1186 (1987).

Perry, et al., "Perry's Chemical Engineering Handbook" (McGraw–Hill, NY 1984).

Pishko, et al., "Amperometric Glucose Microelectrodes Prepared through Immobilization of Glucose Oxidase in Redox Hydrogels," *Anal. Chem.* 63:2268–2272 (1991).

Potts and Guy, "Predicting Skin Permeability," *Pharm. Res.* 9:663–669 (1992).

Prausnitz, et al., "Electroporation of mammalian skin: A mechanism to enhance transdermal drug delivery," *Proc. Natl. Acad. Sci.USA* 90:10504–10508 (1993).

Quillen, W.S., "Phonophoresis: A Review of the Literature and Technique," *Athl. Train.* 15:109–110 (1980).

Robinson & Lee, "Influence of Drug Properties on Design," *Controlled Drug Delivery* 42–43.

Rosell, J., et al., "Skin Impedance From 1 Hz to 1 MHz," *IEEE Trans. Biomed. Eng.* 35:649–651 (1988).

Skauen, et al., "Phonophoresis," *Int. J. Pharm.* 20:235–245 (1984).

Stringfellow, *Clinical Applications of interferons and their inducers*, (Editors, Marcel Dekker, New York, 1986).

Tamada, et al., *Proceed. Intern. Symp. Control. Rel. Bioact. Mater.* 22; 129–130 (1995).

Tocanne, et al., "Lipid lateral diffusion and membrane organization," *FEB* 257:10–16 (1989).

Tyle and Agrawala, "Drug Delivery by Phonophoresis," *Pharm. Res.* 6:355–361 (1989).

*Ulashik, V.S. et al., Ultrasound Therapy (Minsk, Belarus 1983).

Walker and Hadgraft, "Oleic acid—a membrane 'fluidiser' or fluid within the membrane," *Int. J. Pharm.* 71:R1–R4 (1991).

Walmsley, "Applications of Ultrasound in Dentistry," *Ultrasound in Med. and Biol.* 14:7–14 (1988).

Walters, K. A., "Penetration Enhancers and Their Use in Transdermal Therapeutic Systems," *Transdermal Drug Delivery: Developmental Issues and Research Initiatives*, 197–246 (Hadgraft J., Guy, R.H., Editors, Marcel Dekker, 1989).

Wester and Mailbach, "Animal Models for Percutaneous Absorption," *Topical Drug Bioavailability Bioequivalence and Penetration* (Shah and Maibach, Editors, Plenum Press, New York) 333–349, (1993).

Wheatley, et al., "Use of Ussing Chamber for Investigation of Drug Delivery Across Viable Nasal Tissue Membranes," *Proceed. Intern. Symp. Control. Rel. Bioact. Mater.* (Controlled Release Society, Inc. 14:26–27 (1987).

Williams, et al., "On the non–Gaussian distribution of human skin permeabilities," *Int. J. Pharm.* 86:69–77 (1992).

Wilschut, et al., "Estimating Skin Permeation. The Validation of Five Mathematical Skin Permeation Models," *Chemosphere* 30:1275–1296 (1995).

EFFECT OF ELECTRIC FIELD AND ULTRASOUND FOR TRANSDERMAL DRUG DELIVERY

This is a continuation in part of U.S. Ser. No. 08/574,377 entitled "Chemical and Physical Enhancers and Ultrasound for Transdermal Drug Delivery" filed Dec. 18, 1995 by Mark E. Johnson, Samir S. Mitragotri, Daniel Blankschtein and Robert S. Langer.

The United States government has rights in this invention by virtue of National Institute of Health (NIH grant GM44884) to Robert Langer and Army Office Grant No. DAAL03-90-G0218 to James C. Weaver.

BACKGROUND OF THE INVENTION

The present invention generally relates to improved methods for drug delivery and measurement of analyte using ultrasound in combination with application of an electric field.

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, In Percutaneous Absorption: Mechanisms-Methodology-Drag Delivery., Bronaugh, R. L., Maibach, H. 1. (Ed), pp 1–12, Marcel Dekker, New York, 1989. The word "transdermal" is used herein as a generic term. However, in actuality, transport of drugs occurs only across the epidermis where the drug is absorbed in the blood capillaries. When compared to injections, TDD eliminates the associated pain and the possibility of infection. Theoretically, the transdermal route of drug administration could be advantageous in the delivery of many therapeutic proteins, because proteins are susceptible to gastrointestinal degradation and exhibit poor gastrointestinal uptake, proteins such as interferons are cleared rapidly from the blood and need to be delivered at a sustained rate in order to maintain their blood concentration at a high value, and transdermal devices are easier to use than injections.

Ultrasound has been shown to enhance transdermal transport of low-molecular weight drugs (molecular weight less than 500) across human skin, a phenomenon referred to as sonophoresis (Levy, J. Clin Invest. 1989, 83, 2974–2078; Langer, R., In "Topical Drug Bioavailability, Bioequivalence, and Penetration"; pp. 91–103, Shah V. P., M. H. I., Eds. (Plenum: New York, 1993); Frideman, R. M., 'Interferons. A Primer', Academic Press, New York, 1981)). Ultrasound has been shown to create cavitation within the SC, which disorders the lipid bilayers and increases drug transport (Walters, In Transdermal Drug Delivery: Developmental Issues and Research Initiatives, Hadraft, ed. (Marcel Dekker, 1989) pp. 197–233).

U.S. Pat. No. 4,309,989 to Fahim and U.S. Pat. No. 4,767,402 to Kost, et al., disclose various ways in which ultrasound has been used to achieve transdermal drug delivery. Sonophoresis has been shown to enhance transdermal transport of various drugs. Although a variety of ultrasound conditions have been used for sonophoresis, the most commonly used conditions correspond to the therapeutic ultrasound (frequency in the range of 1 MHz–3 MHz, and intensity in the range of 0–2 W/cm$^2$) (Kost, In Topical Drug Bioavailability Bioequivalence and Penetration, pp. 91–103, Maibach, H. I., Shah, V. P. (Ed) Plenum Press, New York, 1993; U.S. Pat. No. 4,767,402 to Kost, et al.).

In spite of these advantages, very few drugs and no proteins or peptides are currently administered transdermally for clinical applications because of the low skin permeability to drugs. Application of therapeutic ultrasound does not induce transdermal transport of high-molecular weight proteins. It is a common observation that the typical enhancement induced by therapeutic ultrasound is less than ten-fold. In many cases, no enhancement of transdermal drug transport has been observed upon ultrasound application. This low permeability is attributed to the stratum corneum (SC), the outermost skin layer which consists of flat, dead cells filled with keratin fibers (keratinocytes) surrounded by lipid bilayers. The highly-ordered structure of the lipid bilayers confers an impermeable character to the SC (Flynn, G. L., In Percutaneous Absorption: Mechanisms-Methodology-Drug Delivery.; Bronaugh, R. L., Maibach, H. I. (Ed), pages 27–53, Marcel Dekker, New York, 1989).

A variety of approaches have been suggested to enhance transdermal transport of drugs. These include: i) use of chemicals to either modify the skin structure or to increase the drug concentration in the transdermal patch (Junginger, et al. In "Drug Permeation Enhancement"; Hsieh, D.S., Eds., pp. 59–90 (Marcel Dekker, Inc. New York 1994; Burnette, R. R. In Developmental Issues and Research Initiatives; Hadgraft J., G., R. H., Eds., Marcel Dekker: 1989; pp. 247–288); ii) applications of electric fields to create transient transport pathways [electroporation] (Prausnitz Proc. Natl. Acad. Sci. USA 90, 10504–10508 (1993); Walters, K. A., in Transdermal Drug Delivery. Developmental Issues and Research Initiatives, Ed. Hadgraft J., Guy, R. H., Marcel Dekker, 1989) or to increase the mobility of charged drugs through the skin [iontophoresis], and iii) application of ultrasound [sonophoresis]. Various approaches including chemical enhancers [Walters, K. A., in Transdermal Drug Delivery: Developmental Issues and Research Initiatives, Hadgraft J., Guy, R. H., Marcel Dekker: New York (1989)], ultrasound [Levy et al., J. Clin. Invest., 83: 2074–2078 (1989); Mitragotri et al., J. Pharm. Sci, 84:697–706 (1995)] and electrical enhancement [Prausnitz et al. Proc. Natl. Acad. Sci. USA, 90:10504–10508 (1993); Pliquett et al., Pharmaceutical Research, 12:549–555 (1995); Chizmadzhev et al., Biophysical J. 68:749–765 (1995); Burnette (1989)] have been suggested to enhance transdermal drug transport. In some cases, high strengths of the physico-chemical forces (for example, electricity, ultrasound) are required to deliver a given drug dose transdermally. However, the highest strength of these physico-chemical forces that can be used is limited by their adverse physiological effects.

Chemical enhancers have been found to increase transdermal drug transport via several different mechanisms, including increased solubility of the drug in the donor formulation, increased partitioning into the SC, fluidization of the lipid bilayers, and disruption of the intracellular proteins (Kost and Langer, In Topical Drug Bioavailability, Bioequivalence, and Penetration; Shah and Maibech, ed. (Plennum, N.Y. 1993) pp. 91–103 (1993)). U.S. Pat. No. 5,445,611 to Eppstein, et al., describes enhancement of ultrasound using the combination of chemical enhancers with modulation of the frequency, intensity, and/or phase of the ultrasound to induce a type of pumping action. However, the intensity and frequencies used in the examples are quite high, which generates heat and decreasing transport over time.

Electroporation is believed to work in part by creating transient pores in the lipid bilayers of the SC (Burnett (1989)). Iontophoresis provides an electrical driving force to move compounds. Electroporation involves application of electric field pulses that create transient aqueous pathways in lipid bilayer membranes, causing a temporary alteration of skin structure. While occurrence of aqueous pores may allow transdermal permeation of neutral molecules by diffusion, the transport of charged molecules during pulsing occurs predominantly by electrophoresis and electroosmosis.

Accordingly, a better selection of ultrasound parameters is needed to induce a higher enhancement of transdermal drug transport by sonophoresis. Moreover, although efficacy to some degree has been observed using ultrasound for transport of other compounds, the efficiency of transport under conditions acceptable to patients has not been achieved.

It is therefore an object of the present invention to provide a method and means for enhancing transdermal transport.

It is a further object of the present invention to provide methods for using ultrasound in combination with other means of enhancement for drug delivery and collection of analyte in an efficient, practical manner.

SUMMARY OF THE INVENTION

Transdermal transport of molecules during sonophoresis (delivery or extraction) can be further enhanced by the application of an electric field, for example, by iontophoresis or electroporation. In a preferred embodiment, the ultrasound is low frequency ultrasound which induces cavitation of the lipid layers of the stratum corneum (SC). This method i) provides higher transdermal fluxes, ii) allows rapid control of transdermal fluxes, and iii) allows drug delivery or analyte extraction at lower ultrasound intensities than required in the absence of an electric field. Still further enhancement can be obtained using a combination of chemical enhancers and/or magnetic field with the electric field and ultrasound.

Examples using two model compounds, calcein and sulphorhodamine, demonstrate that transdermal transport enhancement induced by simultaneous application of ultrasound and electric pulses is higher than that due to electric pulses or ultrasound alone. Application of ultrasound reduces the threshold voltage required for the onset of calcein and sulphorhodamine transport in the presence of electric fields.

DETAILED DESCRIPTION OF THE INVENTION

Figure 1A:
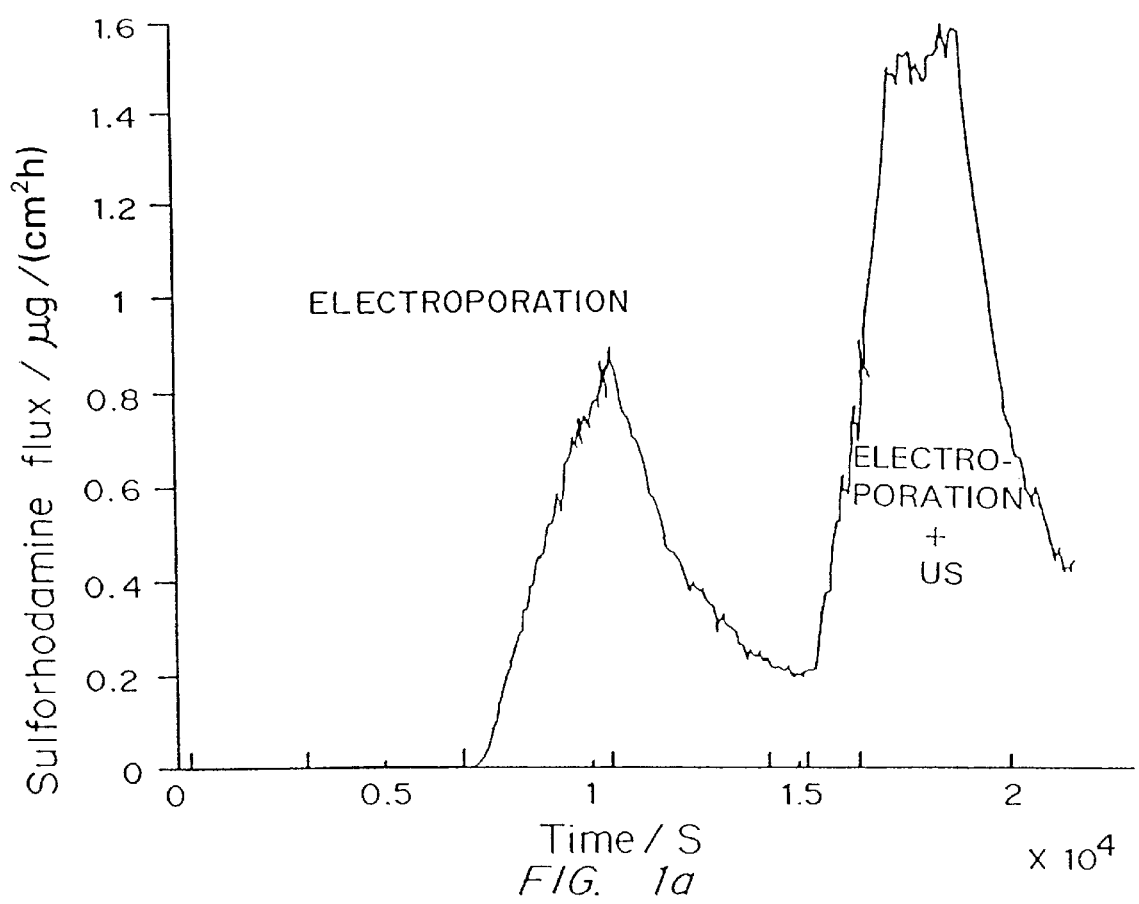
FIG. 1A is a graph of sulforhodamine flux/$\mu$g/(cm$^2$h) over time (seconds) for electroporation of sulforhodamine, followed by application of electroporation in combination with ultrasound. After 400 sec of passive diffusion, pulsed ultrasound (1 MHz, 20% duty cycle, 2.5–2.9 W/cm$^2$) was turned on for 2750 sec. The ultrasound was turned off at 2750 sec. High voltage pulsing was turned on at 6900 sec for 1 hour (10,500 sec end of electroporation pulsing). Ultrasound (1 MHz, 0.8 cm$^2$ 20% duty cycle, 2.5–2.9 W/cm$^2$) was turned on again at 14,310 sec, electroporation was turned on again at 15,200 sec while the pulsed ultrasound was on. At 16,440 sec the ultrasound wave was changed from pulsed to continuous while the electroporation continued.

Sonophoresis:

As used herein, sonophoresis is the application of ultrasound to the skin, alone or in combination with chemical enhancers, iontophoresis, electroporation, magnetic force fields, mechanical pressure fields or electrical fields, to facilitate transport of a compound through the skin. In one embodiment, a drug, alone or in combination with a carrier, penetration enhancer, lubricant, or other pharmaceutically acceptable agent for application to the skin, is applied to the skin. In another embodiment, the compound is an analyte such as glucose which is present in a body fluid and extracted by application of the ultrasound, alone or in combination with other forces and/or chemical enhancers.

Ultrasound is defined as sound at a frequency of between 20 kHz and 10 MHz, with intensities of between greater than 0 and 3 W/cm$^2$. Ultrasound is preferably administered at frequencies of less than or equal to about 2.5 MHz to induce cavitation of the skin to enhance transport. As used herein, "low frequency" sonophoresis is ultrasound at a frequency that is less than 1 MHz, more typically in the range of 20 to 40 KHz, which can be applied continuously or in pulses, for example, 100 msec pulses every second, at intensities in the range of between zero and 1 W/cm$^2$, more typically between 12.5 mW/cm$^2$ and 225 mW/cm$^2$. Exposures are typically for between 1 and 10 minutes, but may be shorter and/or pulsed. It should be understood that although the normal range of ultrasound begins at 20 kHz, one could achieve comparable results by varying the frequency to slightly more or less than 20 kHz. The intensity should not be so high as to raise the skin temperature more than about one to two degrees Centigrade.

Application of low-frequency (20 kHz) ultrasound dramatically enhances transdermal transport of drugs. Transdermal transport enhancement induced by low-frequency ultrasound was found to be as much as 1000-fold higher than that induced by therapeutic ultrasound (frequency in the range of 1 MHz–3 MHz, and intensity in the range of 0–2 W/cm$^2$). Another advantage of low-frequency sonophoresis as compared to therapeutic ultrasound is that the former can induce transdermal transport of drugs which do not passively permeate across the skin. Application of low-frequency ultrasound appears to induce cavitation inside as well as outside the skin. Cavitation occurring at either location may cause disordering of the SC lipids. In addition, oscillations of cavitation bubbles may result in significant water penetration into the disordered lipid regions. This may cause the formation of aqueous channels through the intercellular lipids of the SC. This allows permeants to transport across the disordered lipid domains, then across keratinocytes and the entire SC. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (by a factor of up to 25) than that through the tortuous intercellular lipids in the case of passive transport.

Many ultrasound devices are available commercially which can be used in the method described herein. For example, the ultrasonic devices used by dentists to clean teeth have a frequency of between about 25 and 40 KHz. Commercially available portable ultrasound tooth-brushes make use of a small sonicator contained within the toothbrush (Sonex International Corporation). This sonicator is portable and operates on rechargeable batteries. Small pocket-size sonicators carried by patients and used to "inject" drugs whenever required could be readily adapted from these devices. In addition, these devices could be combined with sensors that can monitor drug concentrations in the blood to formulate a self-controlled drug (insulin, for example) delivery method that can decrease the attention required by the patient.

Devices typically used for therapeutic or diagnostic ultrasound operate at a frequency of between 1.6 and 10 MHz. These devices can also be modified for use at lower frequencies. The devices may optionally include a reservoir for an ultrasound gel, which will typically have a sound coefficient like water, or a reservoir for collecting analyte.

Although principally described herein as the combination of ultrasound with an electrical field, chemical enhancers and physical enhancers can also be used in combination with ultrasound. Physical enhancers, as used herein, in addition to iontophoresis and electroporation, include magnetic fields and mechanical pressure. Ultrasound is used to permeabilize the skin followed by the application of various force fields to provide additional driving force for transdermal transport of molecules.

Electric Fields (Iontophoresis or Electroporation)

Application of ultrasound or electric current alone has been shown to enhance transdermal drug transport and blood analyte extraction. As discussed above, ultrasound-induced cavitation occurring inside or outside the skin causes disordering of the SC lipids. Oscillations of cavitation bubbles may also result in significant water penetration into the disordered lipid regions. This may cause the formation of aqueous channels through the intercellular lipids of the SC, thus allowing permeants to transport across the disordered lipid domains. Once able to diffuse across the lipid domains, molecules may diffuse across keratinocytes and hence across the entire SC.

Application of electric current enhances transdermal transport by different mechanisms. First, application of an electric field provides an additional driving force for the transport of charged molecules across the skin and second, ionic motion due to application of electric fields may induce convective flows across the skin, referred to as electroosmosis. This mechanism is believed to play a dominant role in transdermal transport of neutral molecules during iontophoresis. Iontophoresis involves the application of an electrical current, preferably DC, or AC, at a current density of greater than zero up to about 1 mA/cm$^2$. Typically, a constant voltage is applied since resistance changes over time, usually in the range of between greater than zero and four volts.

Attempts have been made to enhance the skin permeability using electric current to achieve transdermal extraction of glucose, as reported by Tamada, et al., *Proceed. Intern. Symp. Control. Rel. Bioact. Mater.* 22, 129–130 (1995). Although these attempts have been successful to a certain extent, the amounts of glucose extracted by these methods are several orders of magnitude lower than those which could be detected by the currently existing biosensors. The mechanism of sonophoretic transdermal glucose extraction is believed to be similar to that of sonophoretic transdermal drug delivery. Specifically, application of low-frequency ultrasound increases the skin permeability by disordering its lipid bilayers which leads to the formation of aqueous channels through the intercellular lipids of the SC. This allows faster diffusion of glucose present in the interstitial fluids across the permeabilized skin.

The application of ultrasound induces cavitation in the keratinocytes of the stratum corneum. Furthermore, oscillations of cavitation bubbles were shown to induce a partial disorder in the skin lipid bilayer. In view of this, the cumulative effect of ultrasound and electric field may also be related to cavitation induced by ultrasound exposure. In order to test this hypothesis, electric pulses (100 V across the skin, 1 ms exponential pulse applied every minute) and ultrasound (3 MHz, 1.5 W/cm$^2$) were simultaneously applied to skin, as described below. It is known that the cavitational effects vary inversely with ultrasound frequency [Gaertner, W., Frequency dependence of ultrasonic cavitation, *J. Acoust. Soc. Am.,* 26:977–80 (1984)]. No significant cavitational effects have been observed in fluids at high ultrasound frequencies greater than 2.5 MHz. As a result, 2.5 MHz is considered a reasonable estimate of the upper frequency limit for the occurrence of cavitation in fluids at therapeutic ultrasound intensities. Hence, if cavitation plays an important role, the synergistic effect of ultrasound and electric field should be nearly absent when 3 MHz ultrasound is used. Exposure to ultrasound at 3 MHz (intensity=1.5 W/cm$^2$) does not affect transdermal transport by electric field pulsing. These results indicate that cavitation may play a major role in the synergistic effect of ultrasound and electric field pulsing.

Chemical Enhancers.

Lipid Bilayer Disrupting Agents.

Chemical enhancers have been found to increase drug transport by different mechanisms. Chemicals which enhance permeability through lipids are known and commercially available. For example, ethanol has been found to increase the solubility of drugs up to 10,000-fold (Mitragotri, et al. *In Encl. of Pharm. Tech.*: Swarbrick and Boylan, eds. Marcel Dekker 1995) and yield a 140-fold flux increase of estradiol, while unsaturated fatty acids have been shown to increase the fluidity of lipid bilayers (Bronaugh and Maiback, editors (Marcel Dekker 1989) pp. 1–12).

Examples of fatty acids which disrupt lipid bilayer include linoleic acid, capric acid, lauric acid, and neodecanoic acid, which can be in a solvent such as ethanol or propylene glycol. Evaluation of published permeation data utilizing lipid bilayer disrupting agents agrees very well with the observation of a size dependence of permeation enhancement for lipophilic compounds. The permeation enhancement of three bilayer disrupting compounds, capric acid, lauric acid, and neodecanoic acid, in propylene glycol has been reported by Aungst, et al. *Pharm. Res.* 7, 712–718 (1990). They examined the permeability of four lipophilic compounds, benzoic acid (122 Da), testosterone (288 Da), naloxone (328 Da), and indomethacin (359 Da) through human skin. The permeability enhancement of each enhancer for each drug was calculated according to $\epsilon_{e/pg} = P_{e/pg}/P_{pg}$, where $P_{e/pg}$ is the drug permeability from the enhancer/propylene glycol formulation and $P_{pg}$ is the permeability from propylene glycol alone.

The primary mechanism by which unsaturated fatty acids, such as linoleic acid, are thought to enhance skin permeabilities is by disordering the intercellular lipid domain. For example, detailed structural studies of unsaturated fatty acids, such as oleic acid, have been performed utilizing differential scanning calorimetry (Barry *J. Controlled Release* 6, 85–97 (1987)) and infrared spectroscopy (Ongpipattanankul, et al., *Pharm. Res.* 8, 350–354 (1991); Mark, et al., *J. Control. Rel.* 12, 67–75 (1990)). Oleic acid was found to disorder the highly ordered SC lipid bilayers, and to possibly form a separate, oil-like phase in the intercellular domain. SC lipid bilayers disordered by unsaturated fatty acids or other bilayer disrupters may be similar in nature to fluid phase lipid bilayers.

A separated oil phase should have properties similar to a bulk oil phase. Much is known about transport in fluid bilayers and bulk oil phases. Specifically, diffusion coefficients in fluid phase, for example, dimyristoylphosphatidylcholine (DMPC) bilayers Clegg and Vaz In "Progress in Protein-Lipid Interactions" Watts, ed. (Elsevier, N.Y. 1985) 173–229; Tocanne, et al., *FEB* 257, 10–16 (1989) and in bulk oil phase Perry, et al., "Perry's Chemical Engineering Handbook" (McGraw-Hill, N.Y. 1984) are greater than those in the SC, and more importantly, they exhibit size dependencies which are considerably weaker than that of SC transport Kasting, et al., In: "Prodrugs: Topical and Ocular Delivery" Sloan, ed. (Marcel Dekker, N.Y. 1992) 117–161; Potts and Guy, *Pharm. Res.* 9, 663–339 (1992); Willschut, et al., *Chemosphere* 30, 1275–1296 (1995). As a result, the diffusion coefficient of a given solute will be greater in a fluid bilayer, such as DMPC, or a bulk oil phase than in the SC. Due to the strong size dependence of SC transport, diffusion in SC lipids is considerably slower for larger compounds, while transport in fluid DMPC bilayers and bulk oil phases is only moderately lower for larger compounds. The difference between the diffusion coefficient in the SC and those in fluid DMPC bilayers or bulk oil phases will be greater for larger solutes, and less for smaller compounds. Therefore, the enhancement ability of a bilayer disordering compound which can transform the SC lipids bilayers into a fluid bilayer phase or add a separate bulk oil phase should exhibit a size dependence, with smaller permeability enhancements for small compounds and larger enhancements for larger compounds.

A comprehensive list of lipid bilayer disrupting agents is described in European Patent Application 43,738 (1982), which is incorporated herein by reference. Exemplary of these compounds are those represented by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, COOC$_2$H$_4$OC$_2$H$_4$OH, —COOCH(CHOH)$_4$CH$_2$OH, —COOCH$_2$CHOHCH$_3$, COOCH$_2$CH(OR")CH$_2$OR", —(OCH$_2$CH$_2$)$_m$OH, —COOR', or —CONR'$_2$ where R' is —H, —CH$_3$, —C$_2$H$_5$, —C$_2$H$_7$ or —C$_2$H$_4$OH; R" is —H, or a non-terminal alkenyl of about 7 to 22 carbon atoms; and m is 2–6; provided that when R" is an alkenyl and X is —OH or —COOH, at least one double bond is in the cis-configuration.

Solubility Enhancers

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones).

U.S. Pat. No. 4,537,776 to Cooper, incorporated herein by reference contains a summary of prior art and background information detailing the use of certain binary systems for permeant enhancement. European Patent Application 43,738, also describes the use of selected diols as solvents along with a broad category of cell-envelope disordering compounds for delivery of lipophilic pharmacologically-active compounds. A binary system for enhancing metaclopramide penetration is disclosed in UK Patent Application GB 2,153,223 A, consisting of a monovalent alcohol ester of a C8-32 aliphatic monocarboxylic acid (unsaturated and/or branched if C18-32) or a C6-24 aliphatic monoalcohol (unsaturated and/or branched if C14-24) and an N-cyclic compound such as 2-pyrrolidone or N-methylpyrrolidone.

Combinations of enhancers consisting of diethylene glycol monoethyl or monomethyl ether with propylene glycol monolaurate and methyl laurate are disclosed in U.S. Pat. No. 4,973,468 for enhancing the transdermal delivery of steroids such as progestogens and estrogens. A dual enhancer consisting of glycerol monolaurate and ethanol for the transdermal delivery of drugs is described in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 discloses penetration-enhancing compositions for topical application including an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Other chemical enhancers, not necessarily associated with binary systems, include dimethylsulfoxide (DMSO) or aqueous solutions of DMSO such as those described in U.S. Pat. No. 3,551,554 to Herschler; U.S. Pat. No. 3,711,602 to Herschler; and U.S. Pat. No. 3,711,606 to Herschler, and the azones (n-substituted-alkyl-azacycloalkyl-2-ones) such as noted in U.S. Pat. No. 4,557,943 to Cooper.

Some chemical enhancer systems may possess negative side effects such as toxicity and skin irritations. U.S. Pat. No. 4,855,298 discloses compositions for reducing skin irritation caused by chemical enhancer-containing compositions having skin irritation properties with an amount of glycerin sufficient to provide an anti-irritating effect.

Combinations of Lipid Bilayer Disrupting Agents and Solvents

Passive experiments without ultrasound with polyethylene glycol 200 dilaurate (PEG), isopropyl myristate (IM), and glycerol trioleate (GT) result in corticosterone flux enhancement values of only 2, 5, and 0.8, relative to the passive flux from PBS alone. However, 50% ethanol and LA/ethanol significantly increase corticosterone passive fluxes by factors of 46 and 900. These passive flux enhancements were due to (1) the increased corticosterone solubility in the enhancers, and (2) interactions of linoleic acid with the skin. Specifically, linoleic acid increased the corticosterone permeability by nearly 20-fold over that from 50% ethanol alone. Therapeutic ultrasound (1 MHz, 1.4 W/cm$^2$) and the chemical enhancers utilized together produce corticosterone fluxes from PBS, PEG, IM, and GT that are greater than the passive fluxes from the same enhancers by factors of between 1.3 and 5.0, indicating that the beneficial effects of chemical enhancers and therapeutic ultrasound can be effectively combined. Ultrasound combined with 50% ethanol produces a 2-fold increase in corticosterone transport above the passive case, but increase by 14-fold the transport from LA/Ethanol. The combination of increased corticosterone solubility in and permeability enhancement from LA/ethanol and ultrasound yields a flux of 0.16 mg/cm$^2$/hr, 13,000-fold greater than that from PBS alone. The permeability enhancement resulting from the addition of linoleic acid to 50% ethanol exhibits a clear size dependence, with the degree of enhancement increasing with the size of the drug. The degree of permeation enhancement achieved by adding linoleic acid to 50% ethanol and applying ultrasound exhibits a similar size dependence. These results suggest that linoleic acid and therapeutic ultrasound, which are both lipid bilayer disordering agents, shift the transport of lipophilic molecules from the passive regime to a regime with a very weak size dependence.

Mechanical Forces.

Mechanical or Osmotic Pressure

The advantages of combining sonophoresis with physical enhancers is not restricted to electrical current. Effects on transdermal transport may also be observed between ultrasound and pressure (mechanical or osmotic) as well as between ultrasound and magnetic fields since the physical principles underlying the enhancement are believed to be similar or the same. A pressure gradient can be used to enhance convection (physical movement of liquid) across the skin permeabilized by sonophoresis. This can be particularly useful in transdermal extraction of blood analytes. Application of pressure, for example, a vacuum or mechanical pressure, to the skin pretreated by sonophoresis can result in transdermal extraction of interstitial fluid which can be analyzed to measure concentration of various blood analytes.

Magnetic Fields

Application of magnetic fields to the skin pretreated with ultrasound may also result in a higher transport of magnetically active species across the skin. For example, polymer microspheres loaded with magnetic particles could be transported across the skin using sonophoresis and magnetic fields.

The combination of sonophoresis with an electric field, and optionally, any of these additional physical mechanisms for enhanced transport provides the following advantages over sonophoresis or the physical enhancers alone: i) It allows lowering application times to deliver a given drug dose or extract a certain amount of analytes compared to the required times in the presence of ultrasound or one of the other enhancers alone; ii) It reduces the magnitude of the required ultrasound intensity and electric current or pressure to achieve a given transdermal flux compared to that required if, the enhancers were used alone; and iii) It can be used to provide a better control over transdermal transport of molecules compared to that obtained using an enhancer alone.

The combination of electrical field and ultrasound can be applied to any membrane. The membrane can be skin, cell membrane, cell wall and other biological as well as synthetic membranes. The electric fields can be continuous, pulsed, having high as well as low voltage. Application of ultrasound together with the electrical fields results in higher flux compared to the flux observed with electroporation or ultrasound alone. The onset time of transdermal flux during electroporation can also be reduced by simultaneous applications of ultrasound and electroporation. The effect is more pronounced on less-charged molecules which by other enhancing methods are hard to enhance (iontophoresis). The major limitation of electroporation are the high voltages required in order to cause significant effect. By using the combined effects of ultrasound and electroporation, the intensity levels of the electrical fields will be much lower and therefore no or less damage to the membranes will be observed.

Drug Delivery

Drugs to be Administered.

Drugs to be administered include a variety of bioactive agents, but are preferably proteins or peptides. Specific examples include insulin, erythropoietin, and interferon. Other materials, including nucleic acid molecules such as antisense and genes encoding therapeutic proteins, synthetic organic and inorganic molecules including antiinflammatories, antivirals, antifungals, antibiotics, local anesthetics, and saccharides, can also be administered.

The drug will typically be administered in an appropriate pharmaceutically acceptable carrier having an absorption coefficient similar to water, such as an aqueous gel. Alternatively, a transdermal patch such as the one described in the examples can be used as a carrier. Drug can be administered in a gel, ointment, lotion, suspension or patch, which can incorporate anyone of the foregoing.

Drug can also be encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. The microparticles can have diameters of between 0.001 and 100 microns, although a diameter of less than 10 microns is preferred. The microparticles can be coated or formed of materials enhancing penetration, such as lipophilic materials or hydrophilic molecules, for example, polyalkylene oxide polymers and conjugates, such as polyethylene glycol. Liposome are also commercially available.

Administration of Drug.

The drug is preferably administered to the skin at a site selected based on convenience to the patient as well as maximum drug penetration. For example, the arm, thigh, or stomach represent areas of relatively thin skin and high surface area, while the hands and feet are uneven and calloused. In the preferred embodiment, drug is applied to the site and ultrasound and electrical current applied immediately thereafter. Other enhancers can be applied before, during or immediately after the ultrasound. Chemical enhancers are preferable administered during or before ultrasound.

Based on these calculations and the data in the following examples, one can calculate the required dosage and application regime for treatment of a patient, as follows. A typical diabetic patient (70 Kg weight) takes about 12 Units of insulin three times a day (total dose of about 36 Units per day: cited in 'World Book of Diabetes in Practice' Krall, L. P. (Ed), Elsevier, 1988). If each insulin dose was to be delivered by sonophoresis in 1 hour, the required transdermal flux would be 12 U/hour. Note that 1 unit (1 U) of insulin corresponds approximately to 40 mg of insulin. The transdermal patch area used in these calculations is 40 cm$^2$ (the area of a transdermal FENTANYL™ patch [ALZA Corporation]). The donor concentrations used in these calculations are 100 U/ml in the case of insulin (commercially available insulin solution [Humulin]), $3 \times 10^7$ in the case of γ-interferon (typical concentration of interferon solution recommended by Genzyme Corporation), and $3 \times 10^5$ U/ml in the case of erythropoietin [Davis, et al., *Biochemistry*, 2633–2638, 1987].

A typical γ-interferon dose given each time to patients suffering from cancer or viral infections is about $5 \times 10^6$ U [(i) Grups, et al., *Br. J. Med.*, 1989, 64 (3): 218–220, (ii) Parkin, et al., *Br. Med. J.*, 1987, 294: 1185–1186]. Similar doses of α-interferon and β-interferon have also been shown to enhance the immune response of patients suffering from viral infections and cancer (cited in 'Clinical Applications of interferons and their inducers', Ed. Stringfellow D., Marcel Dekker, New York, 1986). If this interferon dose was to be given by sonophoresis in 1 hour, the required transdermal flux would be $5 \times 10^6$ U/hour. Note that 1 unit of γ-interferon corresponds approximately to 1 pg of γ-interferon.

A typical daily erythropoietin dose given subcutaneously to anemic patients is about 400 U (cited in 'Subcutaneous Erythropoietin, Bommer J., Ritz E., Weinreich T., Bommer G., Ziegler T., Lancet, 406, 1988). If this dose was to be delivered in three steps, each involving sonophoresis for 1 hour, the transdermal flux required would be about 140 U/hour. Note that 1 unit of erythropoietin corresponds approximately to 7.6 nanograms of erythropoietin.

Optimal selection of ultrasound parameters, such as frequency, pulse length, intensity, as well as of non-ultrasonic parameters, such as ultrasound coupling medium, can be conducted to ensure a safe and efficacious application using the guidelines disclosed herein as applied by one of ordinary skill in the art.

Measurement of Analytes

Analytes to be Measured.

A variety of analytes are routinely measured in the blood, lymph or other body fluids. Measurements usually require making a puncture in order to withdraw sample. Examples of typical analytes that can be measured include blood sugar (glucose), cholesterol, bilirubin, creatine, various metabolic enzymes, hemoglobin, heparin, vitamin K or other clotting factors, uric acid, carcinoembryonic antigen or other tumor antigens, and various reproductive hormones such as those associated with ovulation or pregnancy. Transdermal drug delivery, in combination with the non-invasive blood analyte measurements, may be used to formulate self-regulated drug delivery methods which provide a close control of the blood concentrations, minimal pain, and better patient compliance. Non-invasive blood analysis method includes extraction of various analytes from the skin's interstitial fluids (where the analytes are present at a concentration proportional to the blood concentration) across the skin into a patch, solution or gel, where their concentration can be measured using biosensors. This method of blood analyte measurements should be particularly useful in the case of diabetic patients who require multiple daily blood glucose measurements.

Measurement of Analytes.

The ultrasound is applied to the skin at the site where the sample is to be collected. A reservoir or collecting container is applied to the site for collection of the sample, which is then measured using standard techniques. The ultrasound conditions are optimized as in the case for drug delivery, to maximize analyte recovery, while maintaining the relative levels of the analyte to other components of the sample. Chemical and/or physical enhancers are applied to the site before, during and after the ultrasound, preferably during or before the ultrasound.

The present invention will be further understood by reference to the following non-limiting examples.

EXAMPLE 1

Comparison of Drug Transfer Through Skin Using Ultrasound or Electrical Field Alone or in Combination Material And Methods A. Materials Full thickness of human cadaver skin (obtained from local hospitals) was heat stripped by immersion in 60° C. water for two minutes followed by the removal of the epidermis. The skin was then stored in a humidified chamber (95% relative humidity) at 4° C. The heat-stripped human epidermis was placed in a custom-made side-by-side permeation chamber, skin area of 0.64 cm$^2$, designed to adapt an ultrasound transducer at the donor side. The donor compartment was filled with a 1 mM solution of calcein (MW 623, electric charge—4; Sigma Chemicals) (CA) and 1 mM sulphorhodamine (MW 607, electric charge—1; Sigma Chemical) (SR) in 150 mM Phosphate Buffer Saline (PBS; Sigma Chemicals).

The ultrasound probe was inserted into the donor compartment. The direction of the ultrasound wave was perpendicular to the membrane surface. The stratum corneum was facing the donor compartment. Both donor and receptor compartments were filled with degassed phosphate buffer saline (PBS) pH=7.4. The temperature was followed to be in the range of 22±2° C. SR and CA were added to the donor compartment to provide concentration of 1 mM CA and 1 mM SR. Fresh PBS was continuously pumped into the receptor compartment at 0.8 ml/min from a reservoir.

B. Fluorescence measurements

The fluorometer was set up for dual wavelength measurements (excitation wavelength=488 nm, emission wavelength=515 nm (calcein), and excitation wavelength=586 nm, emission wavelength=607 nm (sulphorhodamine)).

The sample cuvette of the fluorometer was sealed but for two openings that were provided for the flow of receiver fluid through it. A small custom-made electric stirrer was installed in the cuvette so that there were no stagnant zones in it. Care was taken to avoid any obstruction of the excitation beam by the stirrer. Transdermal calcein and sulphorhodamine flux was calculated from the fluorescence readings by taking into account parameters such as flow rate, receiver compartment volume, and fluorometer caveat volume. The effluent from the receptor compartment was pumped through a spectrofluorometer (Fluorolog-II-system F112AI SPEX-industries, Edison, N.J.) where the fluorescence of calcein and sulphorhodamine was separately measured twice every minute. The excitation for CA is 488 nm and for SR 586 nm, the measurement for CA was at 515 nm and for SR 607 nm. The receptor was mixed by an electromechanical stirrer. The fluorescence measurements were deconvoluted to calculate the CA and SR flux.

C. Application of Ultrasound

Two studies were conducted. In the first, two ultrasound sources were utilized: i. 20 KHz Sonics and Materials (250 W) with a probe surface area of 0.25 cm$^2$. ii. 1 MHz Sonopuls Therapeutic device with probe surface area of 0.8 cm$^2$. Pulsed and continuous modes were evaluated below 2 W/cm$^2$ for the continuous mode and 2–3 W/cm$^2$ pulsed (20% duty-cycle). The distance of the probe tips from the skin was 3 cm for the 20 KHz and 4 cm for the 1 MHz.

In the second study, ultrasound was applied under therapeutically approved conditions (1.4 W/cm$^2$, 1 MHz and 3 MHz, continuous) using a sonicator (Sonopuls 463, Henley International) for various exposure times up to 1 hour. The ultrasound transducer was located at a distance of about 3 cm from the skin.

D. Electroporation

One Ag/AgCl electrode (In vivo metric, Healdsburg, Calif.) was located in the donor and one in the receptor compartment, so that the distance of electrodes from the skin was equal in both the compartments (about 8 mm). Voltage pulses were applied using a pulse generator (ECM 600, BTX, San Diego, Calif.) across the electrodes such that the positive electrode was always in the receptor compartment. This provided an electric driving force for calcein and sulphorhodamine (both negatively charged) to transport across the skin. The voltage applied to the electrodes divides between the saline and the skin. The voltage drop across the skin was estimated using the measured electrical resistance of the skin and saline. The magnitude as well as the length of the voltage pulses was varied over a wide range in order to investigate their effect on transdermal transport.

In the first set of experiments (FIGS. 1A, 1B, 2A), a voltage divider of 10:40 ohm was used to provide a fixed time constant (exponential shape pulse). The maximum pulsing voltage in all experiments was 750 volts across the chamber (refers to a voltage drop across the skin of 210–230 volts). The pulse rate was 1 pulse/min for 60 minutes, controlled by a computer.

In the second set of studies (FIGS. 1C, 2B and 2C, 3), the electric field (100 V) was applied across the skin, exponentially decaying pulse with a time constant ($\tau$) of 1 millisecond, one pulse applied every minute.

In order to assess the stability of these molecules during electroporation, calcein and sulphorhodamine solutions (1 mM each) were exposed to electroporating conditions similar to those used in this study. No difference between the intensity of their fluorescence before and after exposure to electric fields could be detected. In addition, these molecules are stable up to a temperature of 100° C. (measured in terms of fluorescence). When these molecules are degraded, they do not fluoresce. In general, these molecules have been found to be very stable against many physico-chemical changes.

E. Measurements of Passive Electric Skin Properties

A second pair of electrodes (same type as above) was used for monitoring the passive electrical properties (specifically, electrical resistance). Since the electrical resistance of the skin is a good indicator of its barrier properties, the skin resistance was measured before, during and after the experiments. The effect of electroporation and ultrasound separately and together on skin electrical resistance was determined. If the electrical resistivity before the application of either ultrasound or electroporation was lower than 20 k$\Omega$-cm$^2$ or if any significant passive calcein or sulphorhodamine transdermal flux was observed (that is, J greater than 0.002 $\mu$g/cm$^2$/h (the detection limit)), the skin piece was considered leaky and replaced by a new piece.

Results And Discussion

A. Application of Ultrasound Enhances the Efficacy of Electric Field.

The results of the first study are shown in FIG. 1A. FIG. 1A shows the time variation flux of SR which permeated the skin with time. After 400 sec of passive diffusion, pulsed ultrasound (1 MHz, 20% duty cycle, 2.5–2.9 W/cm$^2$) was turned on for 2750 sec. The ultrasound was turned off at 2750 sec. High voltage pulsing was turned on at 6900 sec for 1 hour (10,500 sec end of electroporation pulsing). Ultrasound (1 MHz, 0.8 cm$^2$ 20% duty cycle, 2.5–2.9 W/cm$^2$) was turned on again at 14,310 sec, electroporation (same condition) was turned on again at 15,200 sec while the pulsed ultrasound was on. At 16,440 sec the ultrasound wave was changed from pulsed to continuous while the electroporation continued. The experiment was terminated at 20,040 sec. The experimental procedure is summarized in table 1 below.

TABLE 1

Conditions used for determining effect of ultrasound and electroporation

| From (sec) | To (sec) | Description of the transdermal transport |
|---|---|---|
| 0 | 400 | passive diffusion |
| 400 | 3150 | pulsed ultrasound |
| 3150 | 6900 | passive diffusion |
| 6900 | 10500 | electroporation |
| 10500 | 14310 | passive diffusion |
| 14310– | 15200 | pulsed ultrasound |
| 15200– | 16400 | electroporation + pulsed ultrasound |
| 16440– | 20040 | electroporation + continuous ultrasound |

Figure 1B:
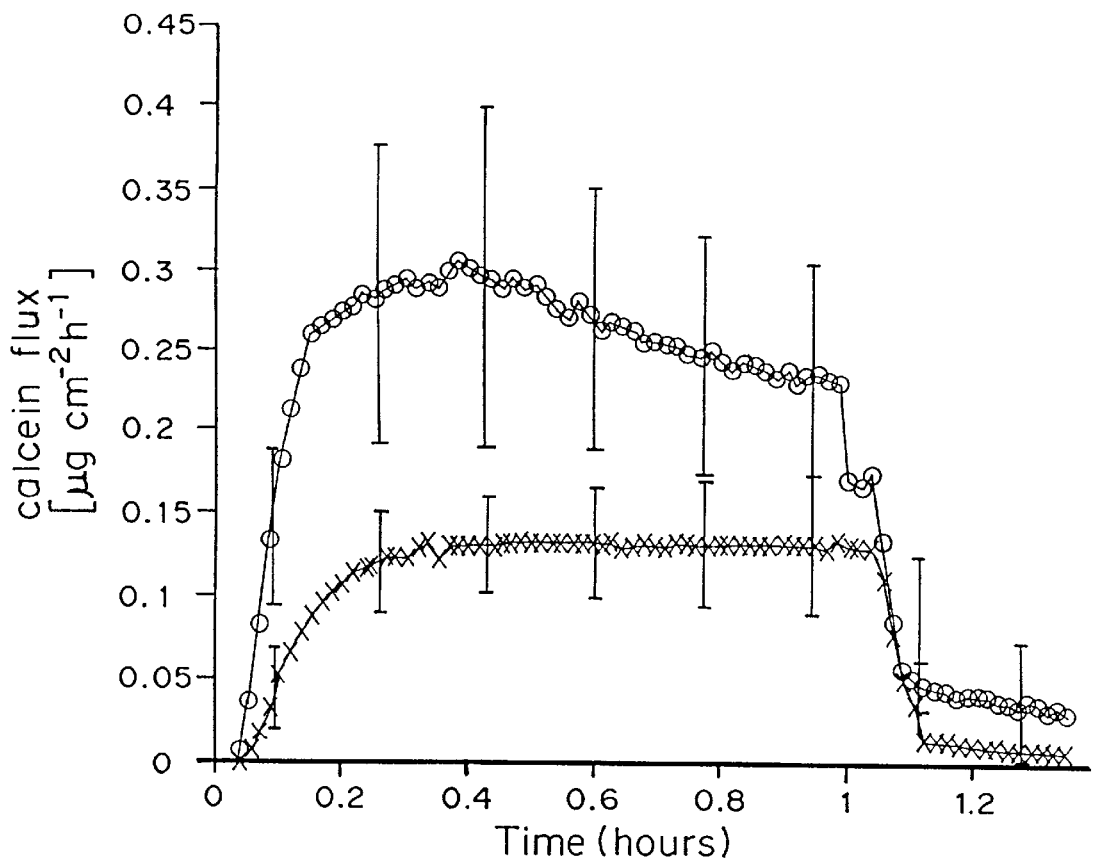
FIG. 1B is a graph of the time variation of calcein flux in the presence of electric fields alone (X) and during simultaneous application of ultrasound and electric field (O) (1 MHz, 1.4 W/cm$^2$, continuous application, and electric field, 100 V across the skin, exponentially decaying pulse with a time constant ($\tau$) of 1 millisecond, one pulse applied every minute). Ultrasound was ON all the time (O). Electric voltage was turned ON at time 0 and was turned OFF at 1 hour in both the case (O as well as X). Presented as means and S.D. of at least three repetitions.
Figure 1C:
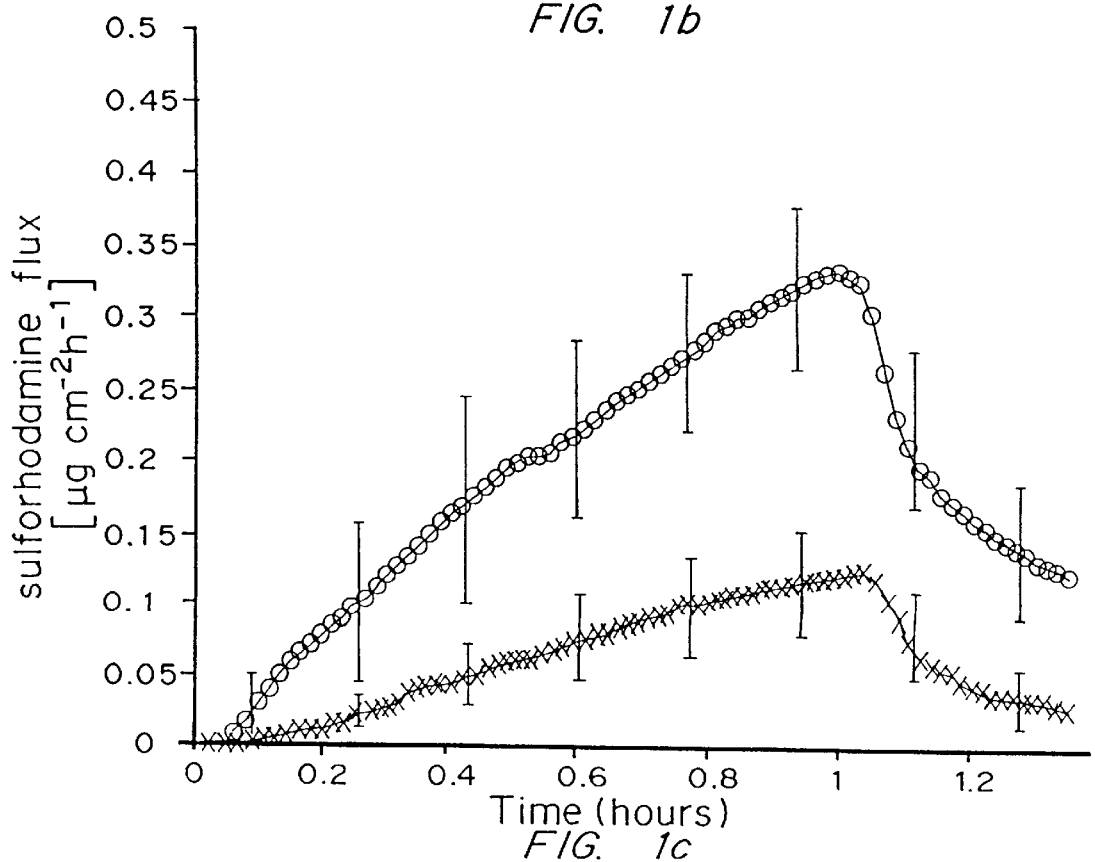
FIG. 1C. Time variation of sulphorhodamine flux in the presence of electric field alone (X) and during simultaneous application of ultrasound and electric field (O) (1 MHz, 1.4 W/cm$^2$, continuous application, and electric field, 100 V across the skin, exponentially decaying pulse with a time constant ($\tau$) of 1 millisecond, one pulse applied every minute). Ultrasound was ON all the time (O). Electric voltage was turned ON at time O and was turned OFF at 1 hour in both the case (O as well as X). Presented as means and S.D. of at least three repetitions.

FIGS. 1B and 1C show the effect of simultaneous application of ultrasound (1 MHz, 1.4 W/cm$^2$, continuous application) and electric field (100 V across the skin, exponentially decaying pulse with a time constant ($\tau$) of 1 millisecond, one pulse applied every minute) on the transdermal transport of calcein and sulphorhodamine respectively. The passive transdermal transport (in the absence of ultrasound and electric field) is below the detection limit and is not shown in FIG. 1B or 1C. Application of ultrasound alone does not enhance the flux of calcein or sulphorhodamine. However, application of ultrasound enhanced steady-state transdermal flux of both calcein and sulphorhodamine during electric field pulsing. The enhancement is quantitatively defined as the amount of calcein or sulphorhodamine transported in the presence of ultrasound-electric field pulsing to that in the presence of electric field pulsing alone. This ratio is 2 in the case of calcein (FIG. 1B), and 3 in the case of sulphorhodamine (FIG. 1C). Application of ultrasound also reduced transdermal calcein transport lag time, defined as the time required to reach the steady state, from a typical value of 15 minutes in the presence of electric field alone to about 9 minutes in the presence of ultrasound and electric field.

Figure 2A:
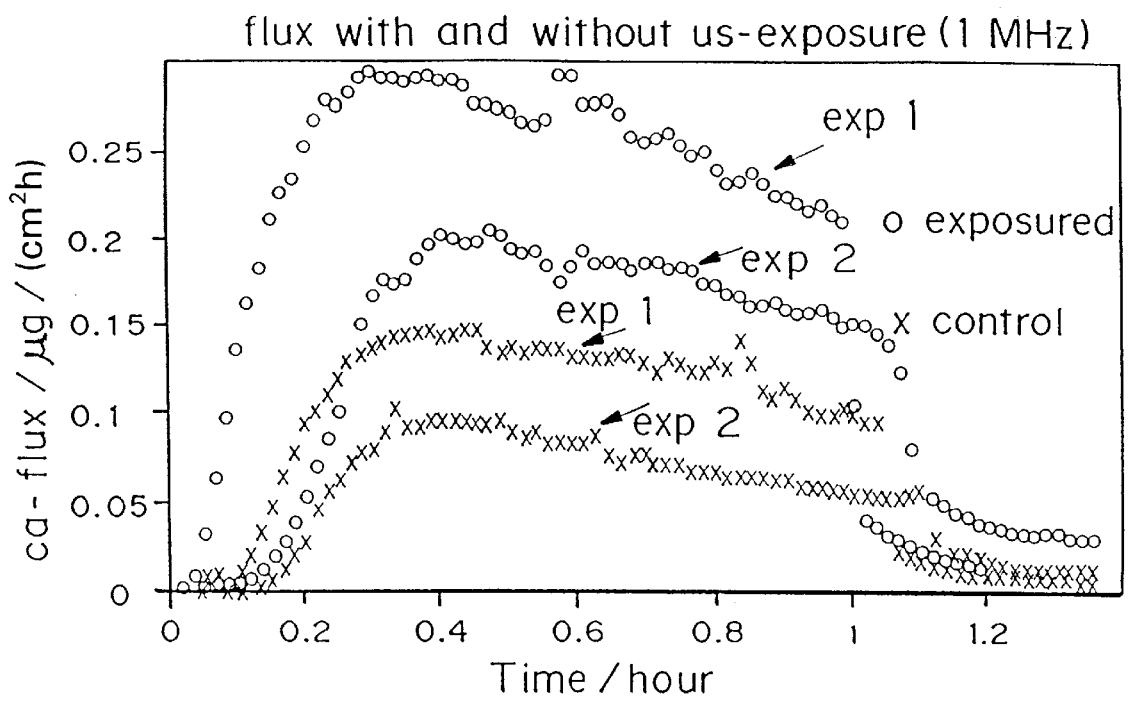
FIGS. 2A and 2B are graphs of calcein and sulphorhodamine flux over time (hours), respectively. Skin samples were exposed continuously to electroporation (electric field (750 V across the chamber, equivalent to approximately 210–230 volts across the skin, exponentially decaying pulse with a time constant ($\tau$) of 1 millisecond, one pulse applied every minute) and continuous ultrasound (1 MHz, 0.8 cm$^2$, 2 W/cm$^2$) (o) and controls (x) where the skin was exposed to electric fields alone.
Figure 2B:
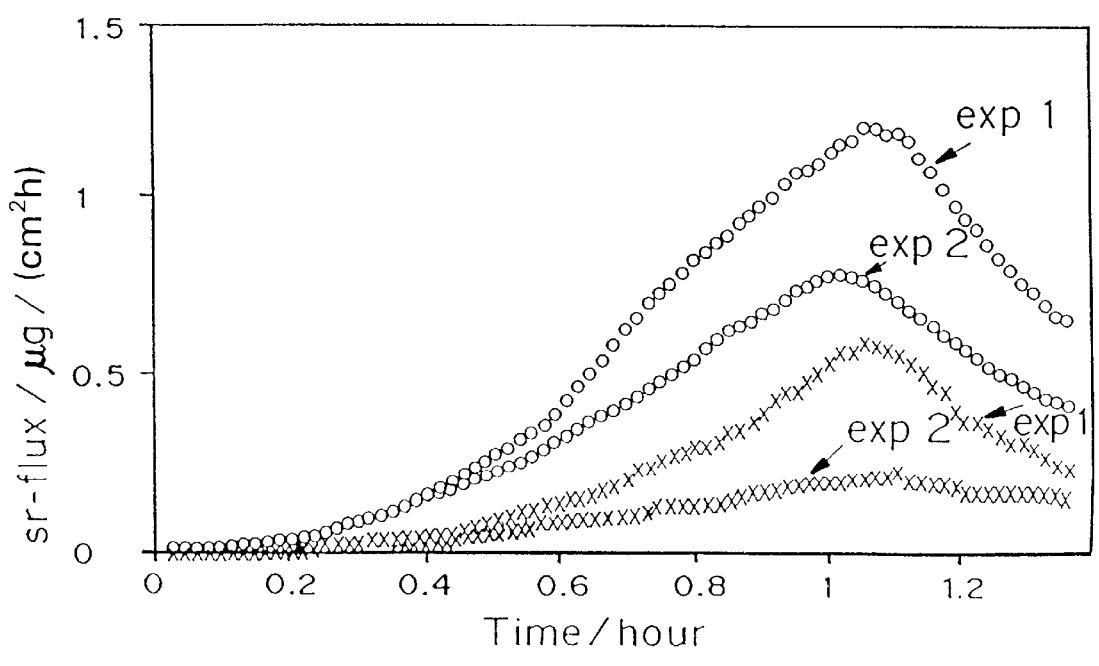

Similar effects of ultrasound on transdermal transport of SR and CA during electroporation can be also seen in FIGS. 2A and 2B which present the flux of CA (FIG. 2A) and SR (FIG. 2B) in experiments where the skin samples were exposed continuously to electroporation and continuous ultrasound (1 MHz, 0.8 cm$^2$, 2 W/cm$^2$) (o) and controls (x) where the skin was exposed to electric fields alone. The possible mechanism for this phenomena might be that the electrical pulsing creates short term pores in the skin while ultrasound is forcing the solutes through these pores.

In order to quantitatively estimate the reduction in the required pulsing voltages by simultaneous application of ultrasound and electric field, transdermal sulphorhodamine transport was measured in the presence as well as absence of ultrasound (1 MHz, 1.4 W/cm$^2$) and electric field (voltage across the skin increased from 20 V to 150 V in steps of 5 V every 30 minutes, 1 millisecond exponential pulse applied every minute).

Figure 3:
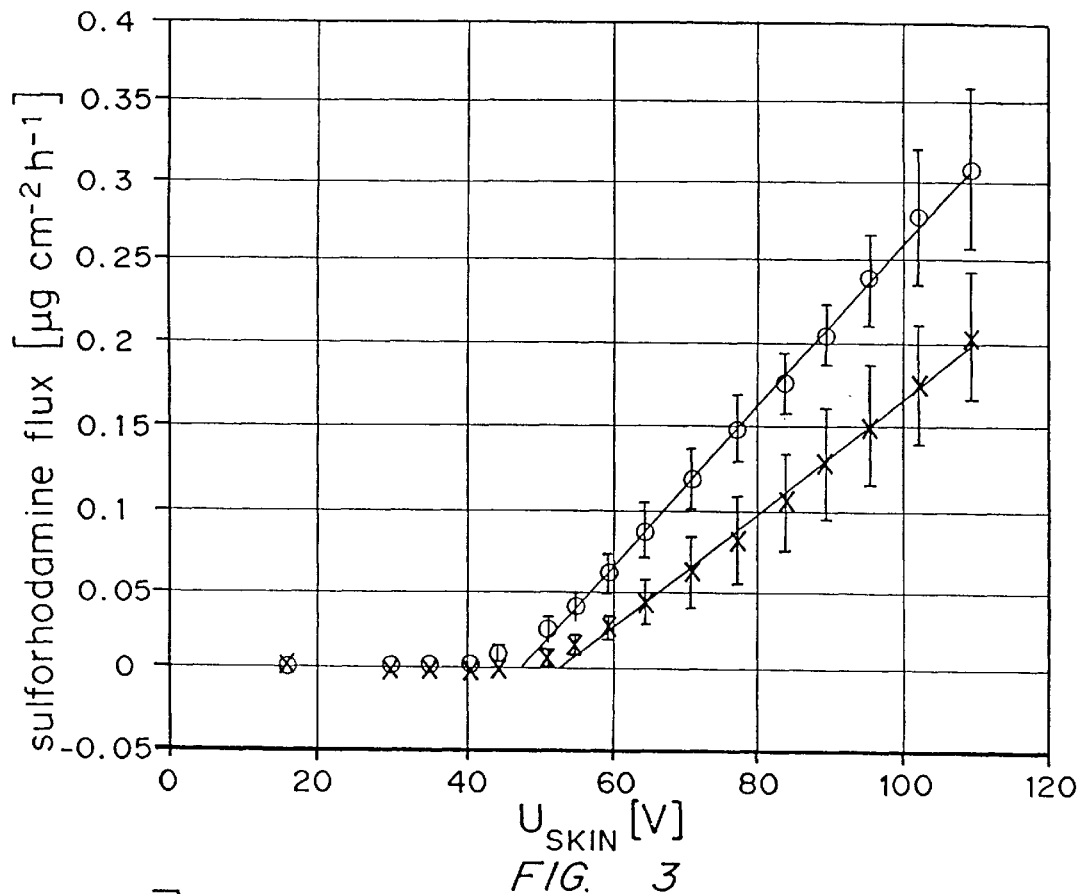
FIG. 3 is a graph of the variation of the transdermal sulphorhodamine flux with the applied electric field (100 V across the skin, exponentially decaying pulse with a time constant ($\tau$) of 1 millisecond, one pulse applied every minute) in the presence (O) and absence (X) of ultrasound. Presented as means and S.D. of at least three repetitions.

FIG. 3 shows the variation of transdermal sulphorhodamine flux with voltage across the skin in the presence (O) as well as in the absence (X) of ultrasound. The transdermal sulphorhodamine flux is nearly zero as long as the voltage is below the threshold value and thereafter increases linearly with voltage. The threshold voltage for this pulsing protocol can be estimated by measuring the intercept of the linear variation of flux with voltage on the voltage axis. In the absence of ultrasound, this threshold is about 53±3 V and that in the presence of ultrasound is about 46±3 V, indicating that application of ultrasound slightly reduces the threshold pulsing voltage. FIG. 3 also shows that the transdermal sulphorhodamine flux at various pulsing voltages is always higher in the presence of ultrasound. Thus, the pulsing voltage required to achieve a given transdermal flux is smaller in the presence of ultrasound. For example, to achieve a transdermal sulphorhodamine flux of 0.15 $\mu$g/cm$^2$/hr, the required voltage is about 95 V in the absence of ultrasound and 75 V in the presence of ultrasound.

Cavitation may play a two-fold role in enhancing the effect of electric field on transdermal transport. First, oscillations of cavitation bubbles induce partial structural disordering of the skin's lipid bilayers. Since the electrical resistance of the disordered bilayers is likely to be smaller than that of the normal lipid bilayers, the applied electric field may concentrate preferentially across the normal bilayers. This may decrease the threshold electroporating voltage for transdermal transport of calcein and sulphorhodamine. Application of ultrasound reduces the threshold pulsing voltage from about 53±3 V in the absence of ultrasound to about 46±3 V in the presence of ultrasound (a reduction of about 12%). This number is comparable to an independent estimate of the fraction of SC bilayer disordered by ultrasound application (15%).

Figure 4:
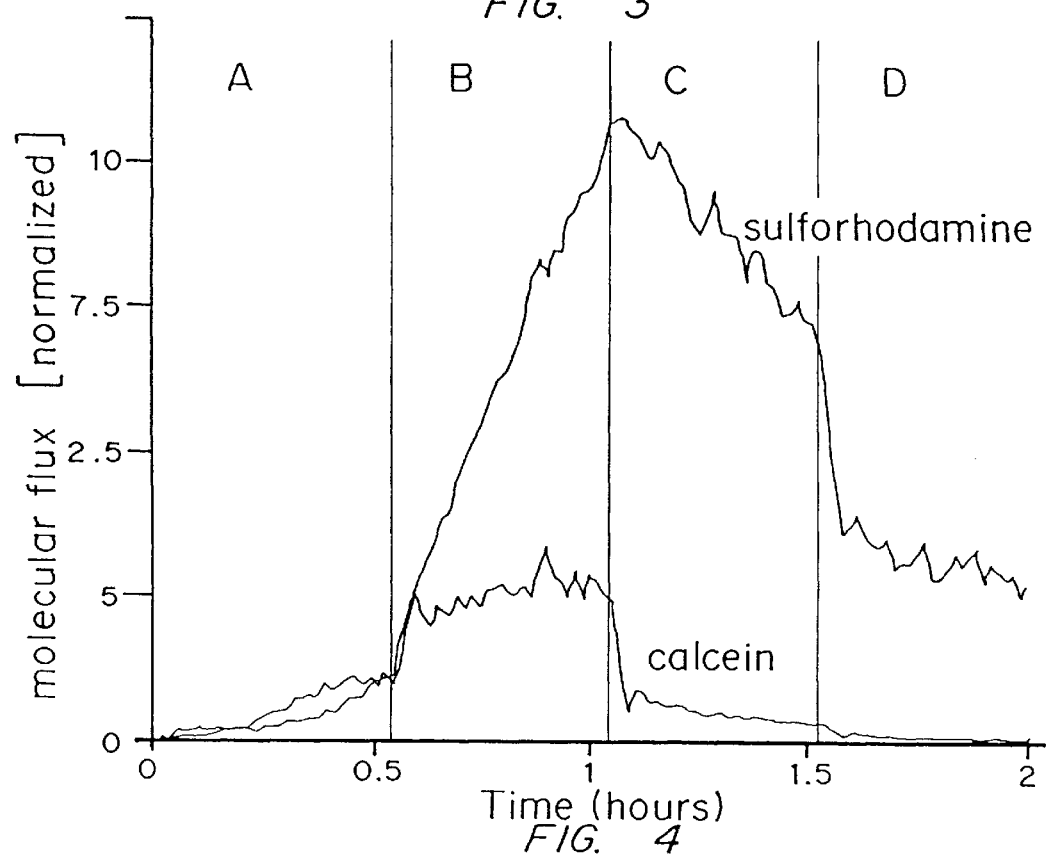
FIG. 4. Variation of the normalized transdermal calcein and sulphorhodamine flux under a variety of conditions. A—in the presence of electric field alone, B—in the presence of ultrasound and electric field, C—in the presence of ultrasound alone, D—in the absence of ultrasound and electric field. The transdermal calcein and sulphorhodamine fluxes have been normalized by the corresponding fluxes prior to application of ultrasound, that is, at the end of 0.5 hours. This was done to assist comparison of the relative charges in transdermal flux under different conditions.

The oscillations of cavitation bubbles may also induce convection across the skin. In order to assess the role of convection in the synergistic effect of ultrasound and electric field, transdermal calcein and sulphorhodamine transport was measured sequentially in the presence of electric field alone, ultrasound and electric field, ultrasound alone and in the absence of ultrasound and electric field. The results of these sequential procedure are shown in FIG. 4. Results from a single experiment are shown to depict the shape of the curves clearly. Note the change in the transdermal flux at 1 and 1.5 hours when electric field and ultrasound is turned OFF respectively. If electrophoresis plays an important role in calcein and sulphorhodamine transport, the transdermal flux is likely to decrease rapidly after electric fields is turned OFF. On the other hand, if cavitation-induced convection plays an important role, transdermal flux would rapidly decrease after turning ultrasound OFF. Indeed, calcein flux decreases rapidly after turning electric field OFF (1 hour) and achieves a value comparable to the background flux. When ultrasound is turned OFF at 1.5 hours, calcein flux further decreases by a small amount (compared to the reduction after turning electric field OFF at 1 hour) and thereafter it remains nearly at the background level. This suggests that calcein transport is mainly driven by electric forces. On the other hand, convection appears to play an important role in transdermal sulphorhodamine transport in the presence of ultrasound and electric field because the sulphorhodamine flux did not decrease rapidly after turning electric fields OFF, but decreased instantaneously after turning ultrasound OFF at 1.5 hours. The total decrease in the transdermal sulphorhodamine flux after turning the electric field OFF (that is, between a period of 1 and 1.5 hours) is comparable to the instantaneous decrease in its value after turning ultrasound OFF at 1.5 hours. This suggests that both electric field and ultrasound-generated convection may play an important role in transdermal sulphorhodamine transport. This difference in the behavior of calcein and sulphorhodamine is presumably because calcein possesses a much larger charge (−4) compared to sulphorhodamine (−1). In this respect, it is important to note that the transdermal transport of calcein and sulphorhodamine in the presence of electric field alone also differs significantly. Calcein transport increases rapidly and achieves a steady state within 15 minutes. Sulphorhodamine flux, however, increases continuously with time over the experimental duration. This difference in the behavior of calcein and sulphorhodamine flux may also be attributed to the lower charge on sulphorhodamine, as the transport during the electrical pulses is driven by electrophoresis.

The combined effect of electroporation and ultrasound on transdermal flux in all experiments was higher for SR than CA, suggesting that the additional enhancement by ultrasound is more effective on less charged molecules. The effect of ultrasound was observed on both the lag time and the steady state flux for the two molecules.

In summary, electroporation of the skin resulted in a very significant increase in SR permeability. The phenomenon was observed also on repeated application of electroporation, but the enhancing effect was only slightly higher. Application of ultrasound without electroporation did not result in enhanced flux. The very pronounced increase in permeability was observed when the skin was exposed to the combined effect of ultrasound and electroporation (more than twice the flux value observed with electroporation without ultrasound). The combined effect of ultrasound and electroporation was also observed in additional exposures of the same skin specimens.

EXAMPLE 2

Determination of Effect of Ultrasound on Skin

The following experiment was measured in order to assess whether application of ultrasound induces any irreversible change in the skin structure. Human skin pieces were exposed to electric field alone (100 V across the skin, exponentially decaying pulse with a time constant (τ) of 1 millisecond, one pulse applied every minute), then simultaneously to ultrasound (1 MHz, 1.4 W/cm$^2$)-electric field and again to electric field alone. A comparison of sulphorhodamine transport due to the electric field alone, before and after the simultaneous electric field-ultrasound treatment, indicated that the flux returns to a near baseline value, suggesting that the application of ultrasound did not induce any irreversible alteration in the barrier properties of skin. The recovery was also supported by electric resistance measurements indicating that application of ultrasound did not cause any irreversible change in the electrical resistance of the skin.

Modifications and variations of the present invention will be obvious to those skilled in the art from the foregoing detailed description, and are intended to come within the scope of the appended claims.

We claim:

1. A method for enhancing transdermal transport of compounds comprising administering to the skin an effective amount of ultrasound at a frequency of less than 2.5 MHz to permeabilize the skin followed by an enhancer selected from the group consisting of electroporation, vacuum or mechanical pressure.

2. The method of claim 1 comprising administering to the skin an effective amount of ultrasound at a frequency of less than 2.5 MHz in combination with electroporation at a voltage of between about 20 V and about 150 V followed by the application of a vacuum or mechanical pressure.

3. The method of claim 1 wherein the ultrasound is administered at a frequency of 1 MHz or less.

4. The method of claim 1 wherein the intensity of the ultrasound is less than the maximum intensity that will not cause permanent skin damage.

5. The method of claim 1 wherein the intensity of the ultrasound is less than 2.5 W/cm$^2$.

6. The method of claim 1 comprising administering to the skin an effective amount of ultrasound at a frequency of less than 2.5 MHz followed by electroporation to effect transdermal transport.

7. The method of claim 1 wherein the ultrasound is followed by administration of vacuumn or mechanical pressure.

8. The method of claim 1 wherein the compound to be transported is a drug the patient is in need of.

9. The method of claim 1 wherein the compound to be transported is an analyte to be measured.

10. The method of claim 1 wherein the ultrasound is pulsed.

* * * * *